(12) United States Patent
Sone et al.

(10) Patent No.: US 7,135,609 B2
(45) Date of Patent: Nov. 14, 2006

(54) NON-HUMAN ANIMAL EXHIBITING BONE METASTASIS OF TUMOR CELLS AND METHOD OF SCREENING FOR BONE METASTASIS INHIBITORS

(75) Inventors: Saburo Sone, Tokushima (JP); Toyokazu Miki, Tokushima (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 178 days.

(21) Appl. No.: 10/143,364

(22) Filed: May 9, 2002

(65) Prior Publication Data

US 2002/0199212 A1 Dec. 26, 2002

Related U.S. Application Data

(63) Continuation-in-part of application No. 09/864,364, filed on May 25, 2001, now abandoned.

(30) Foreign Application Priority Data

May 10, 2001 (JP) .............................. 2001-140538

(51) Int. Cl.
*A01K 67/00* (2006.01)
(52) U.S. Cl. .................... 800/10; 800/8; 800/9; 800/10
(58) Field of Classification Search .................... 800/8, 800/9
See application file for complete search history.

(56) References Cited

U.S. PATENT DOCUMENTS 5,643,551 A * 7/1997 Namikawa et al. ............. 800/3
5,993,817 A * 11/1999 Yoneda et al. ........... 424/158.1

OTHER PUBLICATIONS

Yoneda et al, J Bone Miner Res 2001;16:1486-95.*
Hanbuchi et al, Int J Cancer 1998;78:480-5.*
Lelekakis et al, Clin Exp Metastasis Mar. 1999;17:163-70.*
Miki et al, Oncol Res 2000;12:209-17.*
Fodstad et al, J Cell Biochem 1994;56:23-28.*
Engebraaten et al, Int J Cancer 1999;82:219-25.*
T. Miki et al., "Creation of Models for Multi-Organ Metastases, Including Bone Metastasis, Based on Human Lung Cancer Cell Lines", 9th Meeting of The Japanese Association for Metastasis Research (JAMR), Third Department of Internal Medicine, University of Tokushima, Jun. 29-30, 2000, p. 55.
Arguello, Francisco et al. "A Murine Model of Experimental Metastasis to Bone and Bone Marrow," *Cancer Research*, 48:6876-6881 (1988).
Hall, D. Greg et al., "Effect of the Bisphosphonate Risedronate on Bone Metastases in a Rat Mammary Adenocarcinoma Model System," *Journal of Bone and Mineral Research*, 9 (2):221-230 (1994).
Iguchi, Haruo et al., "An Experimental Model of Bone Metastasis by Human Lung Cancer Cells: The Role of Parathyroid Hormone-related Protein in Bone Metastasis," *Cancer Research*, 56:4040-4043 (1996).
Nakai, Masamichi et al., "A Synthetic Antagonist to Laminin Inhibits the Formation of Osteolytic Metastases by Human Melanoma Cells in Nude Mice," *Cancer Research*, 52:5395-5399 (1992).
Sasaki, Akira et al., "Biphosphonate Risedronate Reduces Metastatic Human Breast Cancer Burden in Bone in Nude Mice," *Cancer Research*, 55:3551-3557 (1995).
Shevrin, Daniel H. et al., "Effect of Etidronate Disodium on the Development of Bone Lesions in an Animal Model of Bone Metastasis Using the Human Prostate Cancer Cell Line PC-3," *The Prostate*, 19:149-154 (1991).
Yano, Seiji et al., " Novel Metastasis Model of Human Lung Cancer in SCID Mice Depleted of NK Cells," *Int. J. Cancer*, 67: 211-217 (1996).

* cited by examiner

*Primary Examiner*—Q. Janice Li
(74) *Attorney, Agent, or Firm*—Finnegan, Henderson, Farabow, Garrett & Dunner, LLP (57) ABSTRACT

The present invention provides a non-human bone metastasis model animal in which tumor cells capable of inducing bone metastasis by peripheral administration have been introduced, and a method for producing the animal. The bone metastasis model animal in the present invention may be useful for understanding the biology of bone metastasis and developing novel therapeutic strategies for lung cancer patient with multi-organ metastases, including bone metastasis. The present invention also provides a method of screening an agent for inhibition and/or prevention of bone metastasis of tumor cells using the non-human bone metastasis model animal.

11 Claims, 8 Drawing Sheets

SEQUENCE LISTING

<160> NUMBER OF SEQ ID NOS: 4

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: PTHrP primer

<400> SEQUENCE: 1
atgcagcgga gagactggtt cag                                          23

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence: PTHrP primer

<400> SEQUENCE: 2
tcaatgcctc cgtgaatcga gctccagagc cgt                               33

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: IL-11 primer

<400> SEQUENCE: 3

```
actgctgctg ctgaagactc ggctgtga                                              28

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: IL-11
      primer

<400> SEQUENCE: 4
atggggaaga gccagggcag aagtctgt                                              28
```

NON-HUMAN ANIMAL EXHIBITING BONE METASTASIS OF TUMOR CELLS AND METHOD OF SCREENING FOR BONE METASTASIS INHIBITORS

This application is a continuation-in-part of U.S. application Ser. No. 09/864,364, filed May 25, 2001 now abandoned, and Japanese Patent Application 2001-140538, filed May 10, 2001, which are herein incorporated by reference for any purpose.

FIELD OF THE INVENTION

The present invention relates to a non-human animal exhibiting bone metastasis of tumor cells, a method for producing the animal, and a method of screening an agent for inhibiting and/or preventing bone metastasis of tumor cells. In particular, the present invention relates to the animal in which tumor cells capable of inducing bone metastasis by peripheral administration have been introduced, and a method for producing the animal. The invention also relates to a method of screening a novel agent, comprising the steps of producing a non-human model animal exhibiting multi-organ metastasis of tumor cells, including bone metastasis, and treating the model animal with the novel agent.

BACKGROUND OF THE INVENTION

Lung cancer is an increasingly common cause of cancer-related death in the world, and over 90% of deaths from lung cancer can be attributed to metastasis (Yano, S. et al., Int. J. Cancer 67:211–217, 1996). Lung cancer is histologically classified into two groups, small cell lung carcinoma (SCLC) and non-small cell lung carcinoma (NSCLC), based on different clinical behavior (the rate of tumor growth, the pattern of tumor progression, the sensitivity to chemo- and radiotherapy). In both types, however, multi-organ metastasis is frequently observed at the time of diagnosis. Bone, following the liver and brain, is the third most common organ of metastasis in lung cancer patients. In particular, bone metastasis causes various severe symptoms by inducing pathological fracture, compression of spinal cord, and hypercalcemia, and reduces the quality of life of the patients (Iguchi, H. et al., Cancer Res. 56:4040–4043, 1996). Though palliative radiotherapy is given to reduce the symptoms for patients with bone metastasis, a novel treatment is necessary for these patients to improve their prognosis.

Recently much attention has been paid to develop a bone metastasis model with human cancer cells in order to understand the molecular mechanism and to develop a treatment. When cancer cells were injected through the intracardiac route into immunodeficient mice, melanoma (Arguello, F. et al., Cancer Res. 48:6876–6881, 1988; Nakai, M. et al., Cancer Res. 52:5395–5399, 1988), breast cancer (Hall, D. G. and Stocia, G., J. Bone Miner. Res. 9:221–230, 1994; Sasaki, A. et al., Cancer Res. 55:3551–3557, 1995), prostate cancer (Shevrin, D. H. et al., Prostate 19:149–154, 1991), and lung cancer (Iguchi, H. et al., Cancer Res. 56:4040–4043, 1996) have been reported to produce bone metastasis.

In these models, tumor cells were injected into the left ventricle of the heart and bone metastasis was developed in 75% of recipient mice. However, intracardiac injection of tumor cells does not seem to be technically easy, and is associated to some extent with sudden death of the animal. Therefore, intracardiac injection of tumor cells imposes a substantial burden on animals, causing ethical and economic problems. As a result, a simple method with good reproducibility of screening a novel agent to solve the important problem, that is, inhibition and/or prevention of bone metastasis, has not yet been developed.

SUMMARY OF THE INVENTION

We have succeeded in producing a bone metastasis model animal, which can be used to elucidate, for example, a mechanism of bone metastasis of tumor cells and develop effective agents for treating and preventing bone metastasis, by peripheral administration of tumor cells.

We examined the abilities of 8 human lung cancer cell lines injected intravenously into natural killer (NK)-cell depleted SCID (severe combined immunodeficient) mice to generate metastatic nodules in bone and multiple organs, and explored the correlation of parathyroid hormone related protein (PTHrP) to the bone metastasis. Though all the cell lines of small cell carcinoma (SBC-5, SBC-3, SBC-3/ADM, H69, H69/VP) formed metastatic nodules in multiple organs (liver, kidney, and lymph nodes), only SBC-5 cells reproducibly developed bone metastases. Squamous cell carcinoma (RERF-LC-AI) cells metastasized mainly into the liver and kidneys, whereas adenocarcinoma (PC14, A549) produced colonies mainly in the lungs. As assessed by X-ray photography, osteolytic bone metastases produced by SBC-5 cells were detected as early as on day 28, and all recipient mice developed bone metastasis by day 35. The expression of PTHrP in 8 cell lines directly correlated with the formation of bone metastasis. No correlation was observed between the formation of bone metastasis and expression other metastasis-related cytokines (IL-1, IL-6, IL-8, IL-10, IL-11, TNF-α, VEGF, M-CSF). Consistent with the formation of bone metastasis by SBC-5 cells, the levels of PTHrP and calcium in the mouse serum were increased in a time-dependent manner, suggesting that PTHrP produced by human lung cancer may play a crucial role in the formation of bone metastasis and hypercalcemia. These results indicate that bone metastasis model of SBC-5 cells may be useful for clarifying the molecular aspects of metastatic process under the different organ microenvironments and developing a treatment for lung cancer patients with bone metastases.

As a result of further studies based on the above findings, we have completed the present invention by finding that by using the above bone metastasis model, a novel agent for inhibiting and/or preventing bone metastasis can be screened.

Therefore, the present invention provides the following (1) to (37):

(1) A non-human bone metastasis model animal exhibiting bone metastasis of tumor cells, in which tumor cells capable of inducing bone metastasis have been introduced by peripheral administration.

(2) The non-human bone metastasis model animal according to 1, wherein the tumor cells are human lung cancer- or breast cancer-derived cells highly expressing PTHrP.

(3) The non-human bone metastasis model animal according to 1, wherein the tumor cells are cells from human lung small cell carcinoma.

(4) The non-human bone metastasis model animal according to 1, which exhibits multi-organ metastasis of tumor cells.

(5) The non-human bone metastasis model animal according to 4, wherein the multi-organ metastases include metastases to one or more organs selected from the group consisting of lung, liver, kidney, and lymph node.

(6) The non-human bone metastasis model animal according to 1, wherein the animal belongs to rodents.

(7) The non-human bone metastasis model animal according to 6, wherein the animal is mouse.

(8) The non-human bone metastasis model animal according to 7, wherein the animal is immnunodeficient mouse.

(9) The non-human bone metastasis model animal according to 8, wherein the animal is SCID mouse.

(10) A method for producing a non-human animal exhibiting bone metastasis of tumor cells, comprising the steps of:
(i) providing a non-human animal having reduced immunity; and
(ii) introducing tumor cells capable of inducing bone metastasis into the animal by peripheral administration.

(11) The method according to 10, wherein the tumor cells are human lung cancer- or breast cancer-derived cells highly expressing PTHrP.

(12) The method according to 10, wherein the tumor cells are cells from human lung small cell carcinoma.

(13) The method according to 10, wherein the step of providing a non-human animal having reduced immunity includes a step of inactivating NK cells in the animal.

(14) The method according to 10, wherein the step of providing a non-human animal having reduced immunity includes a step of reducing the number of NK cells in the animal.

(15) The method according to 10, wherein the step of providing a non-human animal having reduced immunity includes a step of depleting NK cells in the animal.

(16) The method according to 10, wherein the step of providing a non-human animal having reduced immunity includes a step of administering anti-IL-2 receptor antibody to the animal.

(17) The method according to 16, wherein the antibody is anti-IL-2 receptor β-chain antibody.

(18) The method according to 16, wherein the antibody is mouse antibody.

(19) The method according to 10, wherein the step of introducing tumor cells capable of inducing bone metastasis to the animal by peripheral administration includes a step of injecting the tumor cells into the animal intravenously.

(20) The method according to 10, wherein the animal belongs to rodents.

(21) The method according to 10, wherein the animal is mouse.

(22) The method according to 21, wherein the animal is an immunodeficient mouse.

(23) The method according to 21, wherein the animal is SCID mouse.

(24) A method for evaluating efficiencies of treatment against bone metastasis of tumor cells, comprising the step of:
(i) applying a treatment to the non-human bone metastasis model animal according to any one of 1 to 9; and
(ii) comparing the size and/or extent of bone metastasis, and/or symptoms resulted from bone metastasis, with control animal.

(25) A method for determining the effect of a test substance on bone metastasis, comprising the steps of:
(i) administering the test substance to a non-human bone metastasis model animal according to any of 1 to 9; and
(ii) comparing the size and/or extent of bone metastasis, and/or symptoms resulted from bone metastasis, with control animal.

(26) A method of screening a substance for inhibiting and/or preventing bone metastasis of tumor cells, comprising the following steps (i) to (iii):

(i) producing a non-human model animal exhibiting multi-organ metastasis of tumor cells including bone metastasis;
(ii) administering a test substance to the model animal; and
(iii) measuring inhibitory and/or preventive effect of the test substance on bone metastasis.

(27) The method of 26, wherein the non-human model animal is produced by introducing tumor cells capable of inducing bone metastasis into the animal by peripheral administration.

(28) The method of 27, wherein the tumor cells are human lung cancer- or breast cancer-derived cells highly expressing PTHrP.

(29) The method of 28, wherein the tumor cells are cells derived from human small cell lung carcinoma (SCLC).

(30) The method of 26, wherein the animal belongs to rodents.

(31) The method of 30, wherein the animal is a mouse.

(32) The method of 31, wherein the animal is an immunodeficient mouse.

(33) The method of 26, wherein the test substance is a PTHrP antagonist, anti-PTHrP antibody, anti-PTHrP antibody analog or low molecular weight compound.

(34) A method of evaluating efficiencies of treatment against bone metastasis of tumor cells, comprising the following steps (i) and (ii):
(i) treating a non-human model animal exhibiting multi-organ metastasis of tumor cells including bone metastasis; and
(ii) comparing the size and/or extent of bone metastasis, and/or symptoms resulted from bone metastasis, with a control animal.

(35) A method of using a non-human model animal exhibiting multi-organ metastasis of tumor cells including bone metastasis for determining the effect of a test substance on bone metastasis, comprising the following steps (i) and (ii):
(i) administering the test substance to the animal; and
(ii) comparing the size and/or extent of bone metastasis, and/or symptoms resulted from bone metastasis, with a control animal.

(36) A method of producing a medicament for inhibiting and/or preventing bone metastasis of tumor cells, comprising the following steps (i) and (ii):
(i) identifying a substance capable of inhibiting and/or preventing bone metastasis of tumor cells by the screening method of 26; and
(ii) mixing the substance identified in (i) with a pharmaceutically acceptable carrier.

(37) The method of 36, wherein the substance is an anti-PTHrP antibody or anti-PTHrP antibody analog.

BRIEF DESCRIPTION OF THE DRAWINGS

FIG. 1 shows an X-ray photograph of a bone metastasis model mouse of the present invention. 1A indicates osteolytic bone metastases induced mainly in the spine (1B) and bone of extremities (1C).

FIG. 2 shows histological analysis of bone metastasis. Bone metastatic lesions consist of tumor cells with multi-nucleated cells (2A and B).

DETAILED DESCRIPTION OF THE INVENTION

Formation of bone metastasis has been reported to involve various soluble mediators such as cytokines and parathyroid hormone related protein (PTHrP), which was originally identified as a 17 kDa PTH-like adenylate cyclase-stimulating protein derived from a tumor associated with humoral hypercalcemia of malignancy (HHM)(Suva, L. J. et al., Science 237:893–896, 1987; Broadus, A. E. et al., N. Engl. J. Med. 319:556–63, 1988). Interestingly, a variety of tumor cells, including breast cancer, prostate cancer and lung cancer overexpress PTHrP (Burtis, W. J. et al., N. Engl. J. Med. 322:1106–12, 1990). Recently, a highly bone metastatic lung cancer cell line was found to overexpress PTHrP, and that treatment of nude mice with anti-PTHrP antibody inhibited the formation of bone metastasis (Iguchi, H. et al., Cancer Res. 56:4040–4043, 1996), suggesting that PTHrP plays a critical role in the formation of bone metastasis from human lung cancer.

Recently we showed that depletion of NK cells by anti-IL-2 receptor β-chain antibody (TMβ1) in SCID mice resulted in formation of multi-organ metastasis (lung, liver, kidney and lymph nodes) induced by intravenous injections of various human lung cancer cell lines (Yano S., 2 papers). Since there is no report showing the ability of cancer cells injected intravenously into a tail to form bone metastasis in a solid tumor other than those of the haemal system, we examined whether bone metastasis could be produced by 8 different cell lines of human lung cancer injected intravenously in NK-cell depleted SCID mice. Moreover, we also evaluated the correlation of the expression of PTHrP and cytokines with the formation of bone metastasis in human lung cancer cell lines.

The bone metastasis model animal of the present invention refers to a non-human animal exhibiting bone metastasis of tumor cells. In the present invention, the phrase "exhibiting bone metastasis of tumor cells" means the animal carries one or more bone metastases that originated from tumor cells that have been introduced by peripheral administration. Animals that carry metastasis to other organs such as lung, liver, kidney, and lymph node, together with bone metastasis, are also included. In the case of such multi-organ metastasis, effectiveness of the agent for bone metastasis and metastasis to other organs can be examined simultaneously. Although the existence and degrees of bone metastasis in non-human animals can be detected as an image of bone absorption (punch-out image) with X-ray photography and/or identified by means of histological analysis, any means of identification of bone metastasis is within the scope of the invention.

Tumor cells that can be used in the present invention are capable of inducing bone metastasis by peripheral administration. Examples of such tumor cells are those derived from various animals, including human, and include, for example, lung cancer such as squamous cell carcinoma, small cell carcinoma, adenocarcinoma, large cell carcinoma, adenosquamous carcinoma, carcinoid tumor; breast cancer such as noninfiltrating carcinoma, invasive carcinoma (invasive galactophore carcinoma, mucus carcinoma, invasive lobular carcinoma, squamous cell carcinoma and the like); and other cancers such as kidney cancer, prostate cancer, stomach cancer, liver cancer, intestinal cancer, pancreas cancer.

Tumor cells are preferably those highly expressing PTHrP. The term "highly expressing" means herein that PTHrP can be detected at a certain concentration or higher in cell culture supernatant, in particular, in the case of measuring PTHrP C-terminus, that PTHrP can be detected in the concentration higher than that detected in normal individuals. The above term also means that PTHrP can be detected at a certain concentration or higher in blood of non-human animals such as a nude mouse which is implanted with the tumor. For example, the cases where 1.1 pmol/L or higher PTHrP is detected in measuring PTHrP-N terminus (for example, Mitsubishi kagaku Bio-chemical Laboratory Inc.), and where 55.3 pmol/L or higher PTHrP is detected in measuring PTHrP-C terminus (for example, SRL, Inc.) are included in the invention. Further, the term includes the case where 55.3 pmol/L or higher, preferably 100 pmol/L or higher, more preferably 300 pmol/L or higher, yet more preferably 499 pmol/L or higher PTHrP is detected when measuring PTHrP (C-terminus) in cell culture supernatant according to the method described in the Examples below.

In the present invention, human SCLC cell line can be used as particularly suitable cells. Although the human SCLC cell lines SBC-3 and SBC-5 cells which are preferably used were kindly provided by Dr. K. Hiraki (Okayama University, Okayama, Japan), they are also commercially available from Human Science Research Resources Bank (Osaka, Japan). The multi-drug resistant SCLC cell line SBC-3/ADM was established as previously reported (Nakamura, K. et al., Cancer Res. 59:5323–5330, 1999). The human lung squamous cell carcinoma RERF-LC-AI cells were kindly provided by Dr. Akiyama (Radiation Effects Research Foundation, Hiroshima, Japan), but they are also commercially available from RIKEN Cell Bank (Ibaragi, Japan). The human lung adenocarcinoma PC-14 cells, human SCLC cells H69 and its etoposide-resistant variant, H69/VP, were kindly provided by Dr. N. Saijo (National Cancer Center, Tokyo, Japan). The human lung adenocarcinoma PC-14 cells are also commercially available from RIKEN Cell Bank (Ibaragi, Japan), and human SCLC cells H69 are commercially available from ATCC (American Type Culture Collection).

The method for culturing tumor cells may be any method commonly used in the art, and is not limited. For example, SBC-3, SBC-3/ADM and SBC-5 cells can be maintained in Eagle MEM supplemented with 10% heat-inactivated fetal bovine serum (GIBCO, Grand Island, N.Y.) and gentamicin (Schering-Plough, Osaka, Japan) and 4 mM HEPES. The RERF-LC-AI, PC-14, H69 and H69/VP cells can be maintained in RPMI 1640 supplemented with 10% heat-inactivated fetal bovine serum (CRPMI 1640) and gentamicin. All cell lines are preferably incubated at 37° C. in a humidified atmosphere of 5% $CO_2$ in air.

Cells for implanting into animals can be prepared as follows. Tumor cells harvested are washed, for example, with $Ca^{2+}$-and $Mg^{2+}$-free phosphate buffered saline (CMF-PBS). Cell viability can be determined by trypan blue exclusion test, and only single cell suspensions with >90% viability are preferably used.

In the present invention, non-human animals include vertebrate, specifically mammals such as mouse, rat, hamster, guinea pig, rabbit, pig, miniature pig, sheep, cat, and dog, birds such as chicken, and fishes, but any animals other than human are included without any restriction. Animals which belong to rodents, for example, mouse, rat, hamster, and the like, are preferably used in the present invention, and mouse is most preferably used, due to the ease of breeding and manipulation. Any kind of mouse that is used in the art can be suitably used. For example, Male CB-17/IcrCrj-scid mice, ages 6–8 weeks, can be obtained from Charles River Japan, Inc. (Yokohama, Kanagawa, Japan) and maintained under specific pathogen-free conditions throughout the experiment.

The bone metastasis model animal of the present invention can be produced from normal animals. However, more suitable results can be obtained where immunodeficient animals are used. Immunodeficient animals may be obtained or produced by way of known means in the art. For example, SCID mice are commercially available from CLEA Japan Inc. (Meguro, Tokyo, Japan) or Charles River Japan Inc. (Yokohama, Kanagawa, Japan).

The term "peripheral administration" means herein the parenteral administration route by which agents are administered directly into the body, and includes intravenous, intramuscular, intracutaneous, subcutaneous, and intraperitoneal administrations, and does not include percutaneous, inhalation, intracerebral, and ophthalmic administrations.

The bone metastasis model animal of the present invention can be produced, for example, according to a process comprising following steps:

(i) the step of providing a non-human animal having reduced immunity

When implanting heterologous (tumor) cells into animals, it is necessary to reduce (cause deficiency in) host immunological function. Generally, a nude mouse, which lacks T cell function due to a lack of a thymus, or a SCID mouse, which lacks B cell function as well as T cell function, is used as an immunodeficient model for implanting tumor. However, NK cell functions in these models, and NK cell inactivation is required in order to assure a good take of tumor. In that case, asialo-GM1 antibody or TMβ1 treatment employed herein is preferably used. Another method may be that of producing an immuno-suppressed mouse by irradiating X-ray to the whole body of the mouse.

Immunodeficient animals of the present invention include, but are not limited to, rodents, such as a commonly available nude mouse, a nude rat, a SCID mouse, a mouse obtained by administration of asialo-GM1 antibody or TMβ1 into a nude mouse or a SCID mouse, and X-ray irradiated mouse, and the like. Animals that may be used in the present invention also include, but are not limited to, guinea pigs, rabbits, cats, dogs, pigs, sheep, goats, and non-human primates, including monkeys and chimpanzees.

In order to facilitate the metastasis of human lung cancer cell lines, natural killer (NK) cells may preferably be depleted in SCID) mice. The depletion of NK cells may be carried out, for example, by treatment of SCID mice with anti-IL-2 receptor antibodies, especially anti-IL-2 receptor β-chain antibodies (TMβ1). Antibodies can be derived from any kind of animals including human, and mouse antibodies are particularly preferable. Although anti-mouse IL-2 receptor βchain monoclonal antibody, TM-β1(IgG2b), was kindly supplied by Drs. M. Miyasaka and T. Tanaka (Osaka University, Osaka, Japan), it can be produced according to the method described in Japanese Patent No.3040451 (Tanaka, T. et al., J. Exp. Med. 178 1103–1107, 1993). TM-β1 is also available commercially, e.g., from BD Biosciences. For example, TM-β1 Ab (1 mg/1 ml PBS/mouse) may be injected intraperitoneally. into SCID mice 2 days before tumor injection (Yano, S.et al., Int. J. Cancer 67:211–217, 1996).

(ii) the step of introducing tumor cells capable of inducing bone metastasis into the non-human animal by peripheral administration Introduction of tumor cells by peripheral administration can be carried out, preferably by injection, more preferably by intravenous injection. Injection may be performed with 0.3 ml of tumor cells (approximately $1-5 \times 10^6$) into the lateral tail vein of unanesthetized SCID mice pretreated with TM-β1 Ab. After the indicated periods, bone metastasis can be evaluated by X-ray photography (Fuji Film, Tokyo, Japan). To detect the visceral metastases, the mice are sacrificed and the number of metastatic foci on the lungs, liver, kidneys and lymph nodes are counted macroscopically.

For histo-pathological study, the major organs of the animal harvested may be fixed in 10% phosphate-buffered formalin, sectioned and stained with hematoxylin and eosin by standard techniques.

The screening method of the present invention comprises the steps of producing a non-human model animal exhibiting multi-organ metastasis of tumor cells including bone metastasis as described above and administering a test substance, which is a candidate substance for inhibiting and/or preventing bone metastasis, to the non-human model animal. Examples of test substances include, but are not limited to, peptides, proteins, non-peptide compounds, synthetic compounds, fermentation products, cell extracts, and various intracellular factors, and the like. Preferred examples of the test substance include a PTHrP antagonist, anti-PTHrP antibody, anti-PTHrP receptor antibody, anti-PTHrP antibody analog, low molecular weight compound and the like, since anti-PTHrP antibodies have been confirmed to inhibit bone metastasis of PTHrP. Examples of the PTHrP antagonist are those which inhibit the action of PTHrP by binding to PTHrP or PTHrP receptor overexpressed by tumor cells, or promote metabolism. Examples of the anti-PTHrP antibody analog include fragments of the antibody, antibodies modified by gene recombinant techniques, and the like. Examples of the low molecular weight compound include PTHrP (7-34) and the like. The test substance may be administered locally or systemically by oral or parenteral administration known in the art, such as intravenous injection, subcutaneous injection, intraperitoneal injection, and intramuscular injection. The route of administration may be appropriately selected depending on the type of animals used, extent of bone metastasis and the like. The applied dose and dosage time can be appropriately selected according to the type of animal and test substance, extent of bone metastasis, and the like. Alternatively, treatment may be administration of a specified factor in cells, removal of a factor from cells, or reducing the function of a factor. The use of the bone metastasis model animal according to the present invention allows a simple evaluation of whether the test substance is effective or not.

After administration of a test substance, the inhibitory and/or preventive effect of the test substance on bone metastasis is measured. The effect can be measured, for example, by comparing the size and/or extent of bone metastasis, and/or symptoms resulted from bone metastasis, with those in a control animal. Specifically, the effect is preferably measured by an X-ray photograph. The term "control animal" used herein means an animal treated under the same conditions as the subject animal except that the above administration is not performed. Alternatively, the control animal may be the subject animal prior to undergoing administration.

The present invention also provides a method for evaluating efficiencies of treatment against bone metastasis of tumor cells, comprising the following steps:

(i) treating the above non-human bone metastasis model animal; and (ii) comparing the size and/or extent of bone metastasis, and/or symptoms resulted from bone metastasis, with a control animal.

The term "treatment" includes treatment by some agents and radiotherapy, and also includes prevention (inhibition of enlargement) of bone metastasis. When a treatment is effective, contraction, or disappearance, or inhibition of enlargement of bone metastasis can be observed, and relief of some symptoms resulted from bone metastasis, such as paralysis, can also be observed.

Further, the present invention provides a method of using the non-human bone metastasis model animal for determining the effect of a test substance on bone metastasis, comprising the following steps:
(i) administering the test substance to the animal; and
(ii) comparing the size and/or extent of bone metastasis, and/or symptoms resulted from bone metastasis, with a control animal.

An agent that comprises as an active ingredient the test substance for inhibiting and/or preventing bone metastasis of tumor cells may be formulated by any standard method (Remington's Pharmaceutical Science, latest edition, Mark Publishing Company, Easton, USA). The formulation may further comprise pharmaceutically acceptable carriers or additives.

Examples of such carriers and additives include water, pharmaceutically acceptable organic solvents, collagen, polyvinyl alcohol, polyvinyl pyrrolidone, carboxyvinyl polymer, sodium carboxymethyl cellulose, poly(sodium acrylate), sodium arginate, water soluble dextran, sodium carboxymethyl starch, pectin, methyl cellulose, ethyl cellulose, xanthane gum, gum arabic, casein, agar, polyethylene glycol, diglycerin, glycerin, propylene glycol, vaseline, paraffin, stearyl alcohol, stearic acid, human serum albumin (HSA), mannitol, sorbitol, lactose, and surfactants acceptable as pharmaceutical additives.

In practical use, the additive is properly selected from, but is not limited to, the above either alone or in combination depending on the dosage form of the medicament obtained using the present invention. For example, for use as an injectable form, a purified substance for inhibiting and/or preventing bone metastasis is dissolved in a solvent (e.g., physiological saline, a buffer, a glucose solution) and then an adsorption-preventing agent (e.g., Tween 80, Tween 20, a gelatin, human serum albumin) is added thereto. The medicament may also be in a re-constitutable freeze-dried form, which is dissolved before use. For the formulation of the freeze-dried dosage form, an excipient such as a sugar alcohol and a sugar (e.g., mannitol, glucose) may be incorporated.

As described above, we established a novel bone metastasis model animal by intravenous injection of tumor cells, enabling development of a screening method for identifying novel agents and a treatment method for inhibiting and/or preventing bone metastasis using those agents.

The bone metastasis model animals of this invention, particularly those with multiple bone metastases, show symptoms of neurological disorders (paraplesia or monoplesia of the hind leg) and hypercalcemia, which are frequently observed in lung cancer patients with bone metastasis, suggesting that our bone metastasis model seems to reproduce the characteristics of bone metastasis of lung cancer in humans.

The advantages of the model described herein over prior art are 1) the incidence of bone metastases is 100%, 2) the procedure involved is easy, though an immunodeficient animal is preferable to facilitate metastasis formation, 3) since visceral metastasis is also reproducibly developed, antimetastatic effect of drugs in various organs can be evaluated in one model.

The formation of bone metastasis consists of several steps, including tumor-cell arrest at capillaries in bone marrow, extravasation, tumor-cell invasion with bone resorption, and tumor growth. Therefore, various cytokines that modulate these steps can facilitate bone metastasis formation. Pro-inflammatory cytokines (IL-1, IL-6, TNF-α) up-regulate bone resorption and expression of adhesion molecules expressed on the capillaries, and pro-angiogenic cytokines (VEGF and IL-8) can stimulate angiogenesis. In addition, M-CSF and IL-10 can activate macrophages and lymphocytes, respectively, can inhibit tumor growth (Yano, S. et al., Cancer Res. 57: 784–790, 1997; Giovarelli, M. et al., J. Immunology 155: 3112–3123, 1995). Nevertheless, there was no correlation between the expression of these cytokines in human lung cancer cells used and the formation of bone metastasis.

Recently, it was reported that PTHrP-expression in primary tumors directly correlated with the incidence of bone metastasis in breast cancer patients (Powell, G. J. et al., Cancer Res. 51:3059–3061, 1991). In addition, the high level of PTHrP expression was detected in the bone metastases in the patients with breast or prostate cancer (Bundred, N. J. et al., Eur. J. Cancer 28:690–692, 1992; Bouizar, Z. et al., Cancer Res. 53:5076–5078, 1993). Consistent with these reports, highly PTHrP expressing cells had a greater potential to produce bone metastasis in NK-cell depleted SCID mice. Therefore, PTHrP, which stimulates bone resorption, may play a crucial role in the formation of bone metastasis in the model described herein.

Hypercalcemia is frequently observed in lung cancer patients. It can be caused by two different mechanisms, namely HHM (humoral hypercalcemia of malignancy) and LOH (local osteolytic hypercalcemia) (Burtis, W. J. et al., N. Engl. J. Med. 322:1106–12, 1990). HHM is mediated via PTHrP produced by tumor cells. Since PTHrP indirectly stimulates bone resorption by osteoclasts and augments resorption of calcium in the kidneys, the calcium level in the serum is elevated. In LOH, locally produced cytokines (IL-1, IL-6, TNF-α) by tumor cells promote proliferation and differentiation of osteoclast-linage cells, induced bone resorption, and hence cause hypercalcemia (Mundy, G. R., Bone, 12 (suppl.) S1–S6, 1991; Yoneda, T., M. Noda (ed.), Cellular and molecular biology of bone, 375–412, New York, Academic Press, 1993; Jilka, R. L. et al., Science 257:88–91, 1992; Roodman, G. D., Calcif. Tissue Int. 53, S94–S98, 1993; Tamura, T. et al., Proc. Natl. Acad. Sci. USA 90:11924–11928, 1993; Kurihara, N. et al., J. Immunology 144:4226–4230, 1990; Tashjian, Jr A. H. et al., Proc. Natl. Acad. Sci USA 82:4535–4538, 1985; Oreffo, R. O. et al., Biochem. Biophys. Res. Commun. 158:817–823, 1989). In the present study, hypercalcemia was observed in SBC-5-cell injected SCID mice in a time-dependent manner. Tumor cells highly expressed PTHrP at both protein and mRNA levels, whereas no IL-1, IL-6, or TNF-α was detected in the culture supernatants of the cells, suggesting that the hypercalcemia observed in mice injected with these cells may be due to the PTHrP produced by these cells (HHM mechanism).

Interestingly, paralysis, a symptom of bone metastasis, happened in all the mice injected with SBC-5 cells. Nevertheless, paralysis was also observed at lower incidence (10–60%) in mice with bearing SBC-3, SBC-3/ADM, H69, or H69/VP, but the radiolucent lesions (a hallmark of osteolytic bone metastasis) could not be detected by X-ray photography, suggesting that metastases to the brain or spinal cord might be involved in these mice.

The formation of multi-organ metastasis is a critical problem in the management of lung cancer patients. In this study, all 8 human lung cancer cell lines tested developed multi-organ metastases in NK-cell depleted SCID mice. Interestingly, two adenocarcinoma cell lines produced metastases mainly in the lungs, whereas five small cell carcinoma cell lines formed lesions mainly in the liver, kidneys and systemic lymph nodes, resembling their clinical behavior. Although we examined the expression of various cytokines in these cell lines to identify key molecules responsible for organ-specific metastasis, no correlation was observed between cytokine expression and metastatic potential. Of 8 cell lines tested, SBC-5, which overexpresses PTHrP, most aggressively produced metastases into multiple visceral organs (such as the lungs, liver, kidneys and systemic lymph nodes) in addition to bone metastasis. Recent report showed that PTHrP-gene transfection to human prostate cancer cells resulted in resistant to apoptotic stimuli and facilitating tumor growth in vivo (Dougherty, M. K. et al., Cancer Res. 59:6015–6022, 1999). Therefore, PTHrP might facilitate the metastasis formation of SBC-5 cells not only to the bone but also to visceral organs.

In summary, we established the model for bone metastasis by peripheral injection of tumor cells. Our model resembles the characteristics of small cell lung cancer in humans, because the tumor cells produced multi-organ metastasis with osteolytic bone lesions causing paralysis and induced hypercalcemia in recipient mice. In addition, our data suggest that PTHrP, which is secreted by tumor cells, plays a crucial role in the process of bone metastasis and hypercalcemia. Therefore, the bone metastasis model described herein may be useful for understanding the biology of bone metastasis and for developing novel therapeutic strategies for lung cancer patient with multi-organ metastases, including bone metastasis. In addition, the bone metastasis model animals of the present invention may be used in methods of screening agents for efficacy in treatment or prevention of bone metastasis.

EXAMPLES

The present invention is further described in detail in the following Examples, which are not intended to limit the present invention. Moreover, none of materials used in the Examples contained endotoxins, as judged by the limulus amebocyte assay (Seikagaku Kogyo, Tokyo, Japan: minimum detection level, 0.1 ng/ml).

Example 1

Pattern of Metastasis Produced by Human Lung Cancer Cell Lines in NK-cell Depleted SCID Mice We examined the pattern of multi-organ metastasis produced by 8 different human lung cancer cell lines in NK-cell depleted SCID mice. NK-cell depleted SCID mice were injected intravenously through tail vein into the mice with $1–5\times10^6$ tumor cells, and were sacrificed on the day after the indicated periods, and the number of metastatic colonies into the lungs, livers, kidneys and lymph nodes were counted All recipient mice developed tumor lesion and many of the mice became morbid by the time of sacrifice (Table 1).

TABLE 1

Pattern of Metastasis Produced by Human Lung Cancer Cell Lines in NK-Cell Depleted SCID Mice

| Cell Line | Day of Sacrifice | Number of Metastases; median (Range) | | | | |
|---|---|---|---|---|---|---|
| | | Bone | Lungs | Liver | Kidneys | Lymph Nodes |
| Squamous cell carcinoma | | | | | | |
| RERF-LC-AI[a] | day 42 | All 0 | All 0 | 67 (38–100) | 19 (15–30) | 4 (0–18) |
| Adenocarcinoma | | | | | | |
| PC-14[a] | day 28 | All 0 | >100 | 3 (1–7) | 5 (3–13) | 1 (0–3) |
| A549[a] | day 56 | All 0 | >100 | 1 (0–2) | All 0 | 10 (4–14) |
| small cell carcinoma | | | | | | |
| SBC-5[a] | day 35 | 6 (4–9) | 31 (9–38) | 58 (32–84) | 6 (3–20) | 3 (1–4) |
| SBC-3[a] | day 42 | All 0 | All 0 | 12 (7–21) | 12 (10–17) | 13 (6–22) |
| SBC-3/ADM[a] | day 35 | All 0 | All 0 | 54 (41–58) | 1 (0–2) | 4 (2–7) |
| H69[b] | day 56 | All 0 | All 0 | 2 (1–3) | 6 (2–12) | 32 (23–43) |
| H69/VP[b] | day 56 | All 0 | All 0 | 15 (9–16) | 19 (17–25) | 21 (10–28) |

[a]; $1\times10^6$ cells were injected.
[b]; $5\times10^6$ cells were injected.

Squamous cell carcinoma (RERF-LC-AI) cells produced metastatic colonies mainly in the liver and kidneys. Adenocarcinoma PC-14 and A549 cells formed metastases mainly in the lungs. Four out of 5 small cell carcinoma cell lines (SBC-3, SBC-3/ADM, H69 and H69/VP) developed metastases mainly in the liver, kidneys and systemic lymph nodes. Among these cell lines, only one cell line of small cell lung cancer (SBC-5) developed metastasis in bones as well as other organs such as lungs, liver, kidneys and systemic lymph nodes. Paralysis (paraplesia or monoplesia in the hind leg) was occasionally observed in the recipient mice bearing bone metastasis of SBC-5.

Example 2

X-ray and Histological Analysis of Bone Metastasis Produced by SBC-5 Cells

Figure 1A:
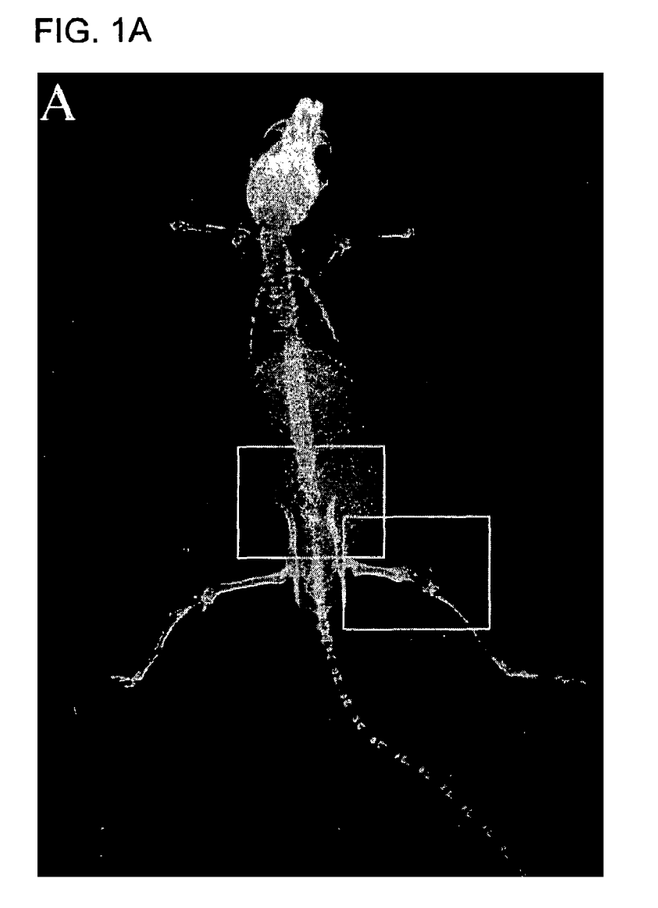
Figure 1B:
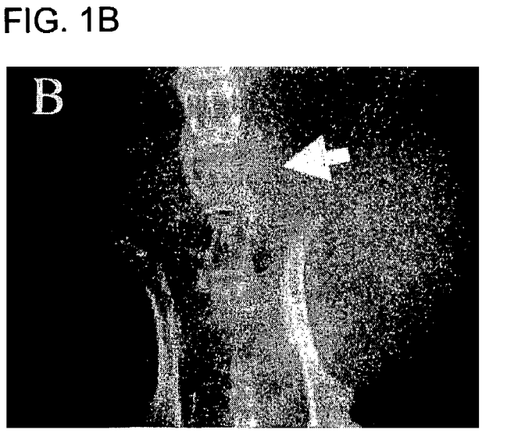
Figure 1C:
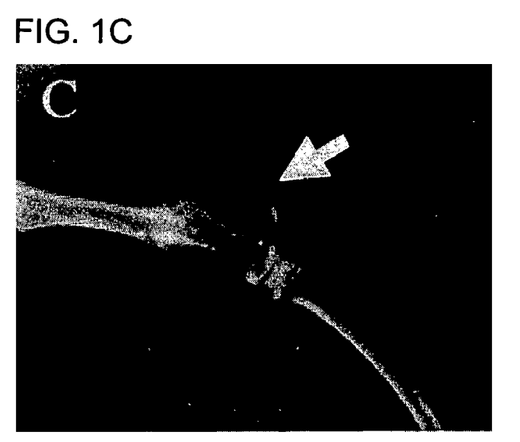
Figure 2A:
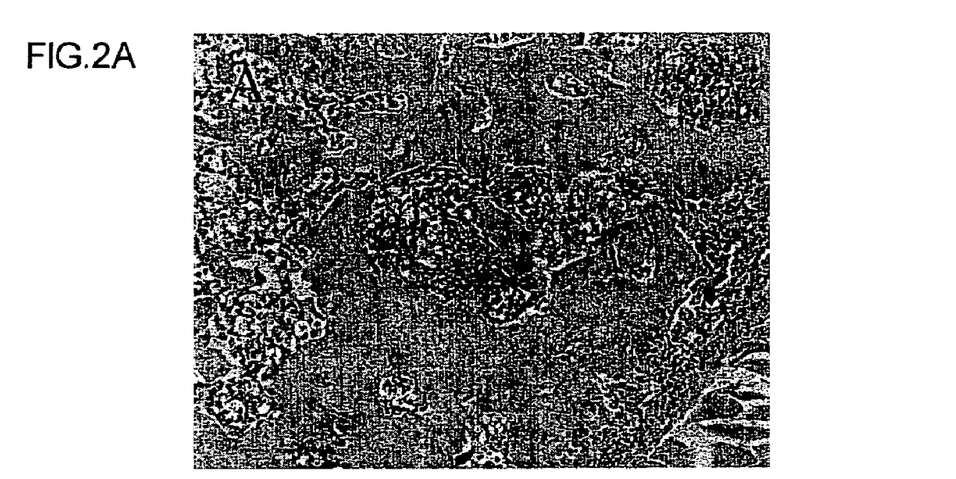
Figure 2B:
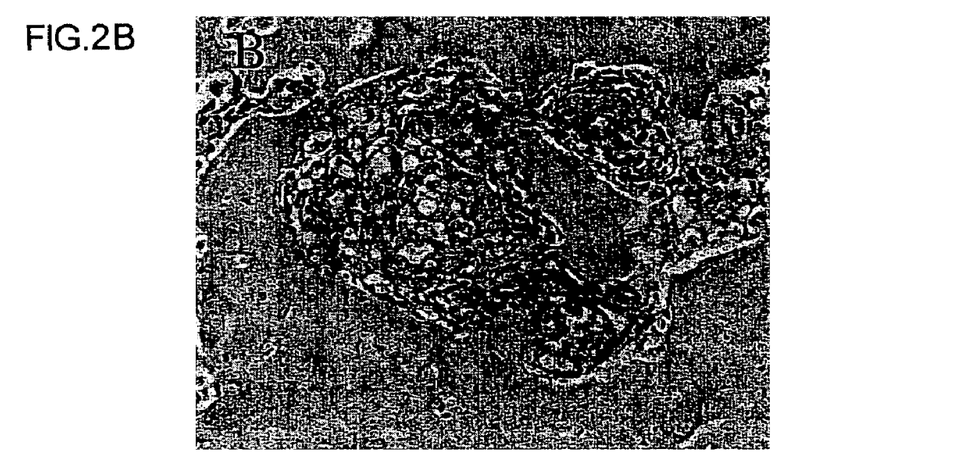

Bone metastases obtained in Example 1 were detected by X-ray photography. Multiple bone metastases were reproducibly developed in the mice injected intravenously with SBC-5 cells and bone metastasis lesions were detected as radiolucent lesions on X-ray photograph (FIG. 1A), indicating osteolytic bone metastases mainly in the spine (FIG. 1B) and bone of extremities (FIG. 1C). Histological analysis shows that these lesions consist of tumor cells with multinucleated cells (FIGS. 2A and B). The mice with these lesions had paralysis of hind legs and urinary retention with enlarged bladder, probably due to pathological fracture and/or compression of spinal cord caused by bone metastasis.

Example 3

Effect of Tumor-cell Number on Bone Metastasis in NK-cell Depleted SCID Mice To determine the optimal experimental conditions for bone metastasis, we injected various numbers of SBC-5 cells into NK-cell depleted SCID) mice. When the mice became moribund, the mice were sacrificed and the number of bone metastasis was determined by X-ray photography. The number of visceral organs was determined macroscopically. The number of bone metastases, as well as visceral metastases, depended on the number of cells injected (Table 2). Based on these results, $1 \times 10^6$ SBC-5 cells were injected in subsequent experiments.

TABLE 4

The Kinetics of Body Weight and Levels of Calcium and PTHrP of NK-Cell Depleted SCID Mice Injected with SBC-5 Cells

| Day of Sacrifice | Body Weight (g) Med. | Range | Ca (mg/dl) Med. | Range | PTHrP (p/mol/l) Med. | Range |
|---|---|---|---|---|---|---|
| 10 | 21.57 | 20.1–23.8 | 8.0 | 8.0–8.2 | 24.1 | <10.0–63.2 |
| 14 | 22.50 | 21.2–23.8 | 9.2 | 9.0–10.4 | 88.2 | 26.3–143 |
| 21 | 21.92 | 21.7–26.0 | 9.6 | 9.2–10.5 | 95.3 | <10.0–115 |

TABLE 2

Pattern of Multiple Organ Metastases Produced by SBC-5 Cells in NK-Cell Depleted SCID Mice

| Number of Injection | Day of Sacrifice | Bone Inc.[a] | Med.[b] | Range | Lungs Inc. | Med | Range | Liver Inc. | Med | Range | Kidneys Inc. | Med | Range | Lymph Nodes Inc. | Med | Range |
|---|---|---|---|---|---|---|---|---|---|---|---|---|---|---|---|---|
| $1 \times 10^5$ | 121 | 3/5 | 3 | 0–6 | 0/5 | 0 | All 0 | 5/5 | 30 | 7–45 | 0/5 | 0 | All 0 | 2/5 | 3 | 0–5 |
| $5 \times 10^5$ | 49 | 5/5 | 6 | 1–8 | 2/5 | 3 | 0–10 | 5/5 | 25 | 14–50 | 3/5 | 2 | 0–4 | 3/5 | 2 | 0–3 |
| $1 \times 10^6$ | 35 | 5/5 | 4 | 2–5 | 5/5 | 5 | 3–18 | 5/5 | 47 | 25–58 | 5/5 | 2 | 1–3 | 5/5 | 2 | 1–3 |
| $2 \times 10^6$ | 35 | 5/5 | 4 | 3–6 | 5/5 | 11 | 9–24 | 5/5 | 49 | 33–84 | 5/5 | 9 | 7–10 | 5/5 | 3 | 2–5 |

[a], Inc., incidence;
[b] Med., median.

Example 4

Time Kinetics of Bone and Visceral Metastases Produced by SBC-5 Cells

We next explored the kinetics of bone metastasis formation by SBC-5 cells. Twenty-five SCID mice depleted of NK cells were intravenously injected with $1 \times 10^6$ SBC-5 cells, and the formation of bone metastasis was examined by X-ray photography on days 10, 14, 21, 28 and 35. Four to five mice were sacrificed at each point to determined visceral organ metastasis. Bone metastasis was detected as early as on day 28 and was observed in all recipient mice on day 35 (Table 3). Consistent with bone metastasis formation, loss of body weight was observed as early as on day 28 (Table 4). On the other hand, metastases to the lung and liver were developed by day 21, and metastases to the kidneys and lymph nodes were produced by day 28. On day 35, all mice developed metastatic lesions into multiple organs, such as the lungs, liver, kidneys and lymph nodes.

TABLE 4-continued

The Kinetics of Body Weight and Levels of Calcium and PTHrP of NK-Cell Depleted SCID Mice Injected with SBC-5 Cells

| Day of Sacrifice | Body Weight (g) Med. | Range | Ca (mg/dl) Med. | Range | PTHrP (p/mol/l) Med. | Range |
|---|---|---|---|---|---|---|
| 28 | 18.64 | 16.6–21.3 | 9.9 | 9.0–10.2 | 299.0 | 146–527 |
| 35 | 16.00 | 13.3–18.4 | 12.0 | 9.5–15.0 | 544.3 | 317–1020 |

The level of calcium in the mouse serum was determined using methylxylenol blue as a substrate for luminescence (Ohtsuka Pharmaceutical Co., Tokushima, Japan).

TABLE 3

Time Kinetics of Multiple Organ Metastases Produced by SBC-5 in NK-Cell Depleted SCID Mice

| Day of Sacrifice | Bone Inc.[a] | Med[b]. | Range | Lungs Inc. | Med | Range | Liver Inc. | Med | Range | Kidneys Inc. | Med | Range | Lymph Nodes Inc. | Med | Range |
|---|---|---|---|---|---|---|---|---|---|---|---|---|---|---|---|
| 10 | 0/25 | 0 | All 0 | 0/4 | 0 | All 0 | 0/4 | 0 | All 0 | 0/4 | 0 | All 0 | 0/4 | 0 | All 0 |
| 14 | 0/21 | 0 | All 0 | 0/4 | 0 | All 0 | 0/4 | 0 | All 0 | 0/4 | 0 | All 0 | 0/4 | 0 | All 0 |
| 21 | 0/17 | 0 | All 0 | 4/4 | 18 | 1–21 | 4/4 | 6 | 5–8 | 0/4 | 0 | All 0 | 0/4 | 0 | All 0 |
| 28 | 8/13 | 2 | 0–4 | 5/5 | 17 | 8–34 | 5/5 | 57 | 34–87 | 5/5 | 5 | 3–13 | 2/5 | 1 | 0–2 |
| 35 | 8/8 | 6 | 4–9 | 8/8 | 31 | 9–38 | 8/8 | 58 | 32–84 | 8/8 | 6 | 3–20 | 8/8 | 3 | 1–4 |

[a], Inc., incidence;
[b], Med., median.

Example 5

Expression of PTHrP and Metastasis-related Molecules in Human Lung Cancer Cell Lines PTHrP and IL-11 have been reported to play a crucial role in bone resorption and bone metastasis (20–27). We determined whether expression of PTHrP and IL-11 in the human lung cancer cell lines correlated with their potential to produce bone metastasis. Tumor cells $5\times10^5$) cells were incubated in CRPMI1640 for 24 hr, and the supernatants were harvested. The level of PTHrP in culture supernatants and mouse serum can be determined using a radioimmuno assay (Ohtsuka Pharmaceutical Co., Tokushima, Japan). The levels of cytokines (VEGF, IL-6, IL-8, IL-10, M-CSF) in the culture supernatants were measured by ELISA (Ohtsuka Pharmaceutical Co. Tokushima, Japan).

Polymerase chain reaction (PCR) analysis was carried out as follows. First-strand cDNA was synthesized from 1 μg total RNA using a RNA LA PCR Kit (Takara Shuzo, Tokyo, Japan) in 20 μl of reaction mixture, according to the manufacture's instructions. The synthesized first-strand cDNA (20 μl) was amplified by polymerase chain reaction (PCR) in a final volume of 100 μl containing 1×LA PCR Buffer II, 2.5 mM $MgCl_2$, 20 pmol of each primer, and 2.5 U of TaKaRa LA Taq polymerase RNA LA PCR Kit (Takara Shuzo, Tokyo, Japan). Sequences of PTHrP primers used were 5'-ATG CAG CGG AGA GAC TGG TTC AG-3' (SEQ ID NO: 1) as a sense strand and 5'-TCA ATG CCT CCG TGA ATC GAG CTC CAG AGC CGT-3' (SEQ ID NO: 2) as an antisense strand (Walsh, C. A. et al., Bone and Mineral 27 43–50, 1994). PCR amplification of PTHrP cDNA was performed under the following conditions: 30 cycles, each cycle comprising 30 sec at 94° C., 30 sec at 58° C., 30 sec at 72° C. Before the first cycle, a denaturation step for 2 min at 94° C. was included, and after 30 cycles the extension was prolonged for 7 min at 72° C. (Walsh, C. A. et al., Bone and Mineral 27 43–50, 1994). Sequences of IL-11 primers used were 5'-ACT GCT GCT GCT GAA GAC TCG GCT GTG A-3' (SEQ ID NO: 3) as a sense strand and 5'-ATG GGG AAG AGC CAG GGC AGA AGT CTG T-3' (SEQ ID NO: 4) as an antisense strand (Auernhammer, C. J. and Melmed, S., Endocrinology 140:1559–1566, 1999). PCR amplification of IL-11 cDNA was performed under the following conditions: 40 cycles, each cycle comprising 30 sec at 94° C., 30 sec at 58° C., 45 sec at 72° C. Before the first cycle, a denaturation step for 2 min at 94° C. was included, and after 30 cycles the extension was prolonged for 3 min at 72° C. (Auernhammer, C. J. and Melmed, S., Endocrinology 140:1559–1566, 1999). PCR products were analyzed by 1.5% agarose gel electrophoresis and visualized by ethidium bromide staining with UV light.

Figure 3:
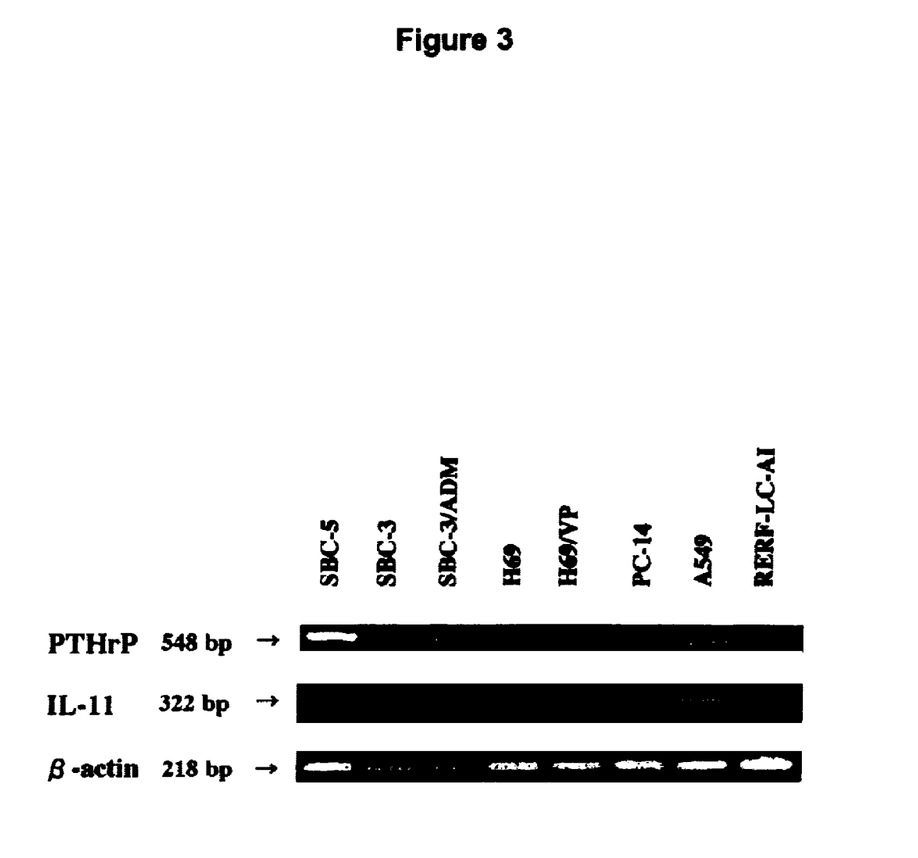
FIG. 3 shows mRNA expression of PTHrP and IL-11 in various tumor cells.

As a result, all the eight cell lines tested expressed IL-11 mRNA, but there was no discernible differences in IL-11 mRNA expression among 8 cell lines (FIG. 3). On the other hand, 6 out of 8 cell lines expressed PTHrP mRNA and the strongest expression was observed in SBC-5 cells. Consistent with mRNA expression, SBC-5 cells secreted more than 10 times higher levels of PTHrP protein compared to other cell lines (Table 5), indicating direct association of the expression of PTHrP and bone metastasis in human lung cancer cells. Data shown are the results of three sets of independent experiments.

TABLE 5

Cytokine Production of Human Lung Cancer Cell Lines

|  | PTHrP[a] | VEGF[b] | IL-6[b] | IL-8[b] | M-CSF[b] | IL-10[b] |
|---|---|---|---|---|---|---|
| RERF-LC-AI | <10 | 1142 | 67 | 1025 | 454 | <20 |
| PC-14 | 15.1 | 11429 | 106 | 236 | 911 | <20 |
| A549 | 30.8 | 743 | <20 | 576 | 89 | <20 |
| SBC-5 | 499 | 2040 | <20 | <20 | <20 | <20 |
| SBC-3 | 19.6 | 1106 | <20 | 13061 | 297 | <20 |
| SBC-3/ADM | 14.4 | 1591 | <20 | 16502 | 310 | <20 |
| H69 | <10 | 3344 | <20 | <20 | <20 | <20 |
| H69/VP | <10 | 3273 | <20 | <20 | <20 | <20 |

[a]; 10 pmol/L
[b]; pg
Data shown are the representation of three sets of independent experiments.

Example 6

Levels of PTHrP and Calcium in the Serum of SBC-5 Cell-bearing Mice

PTHrP has been reported to be responsible for hypercalcemia in HHM (humoral hypercalcemia of malignancy). We evaluated the levels of PTHrP and calcium in the sera of SBC-5 cell-bearing mice. The levels of serum calcium and PTHrP were increased in a time-dependent manner, indicating direct correlation of bone metastasis (or tumor burden) and levels of these markers and loss of body weight (Table 4). These phenomena reflect clinical patients of human lung cancer with bone metastasis.

Example 7

Abilities of Lung Cancer Cells to Produce Cytokines Related to Bone Metastasis

We also examined abilities of lung cancer cells to produce bone metastasis-related cytokine such as IL-1α, IL-6, TNF-α, IL-10, M-CSF, VEGF and IL-8. Although 8 cell lines secreted various levels of these cytokines (Table 5), there was no correlation between the expression level of these cytokines and formation of bone metastasis.

Example 8

Test for Drug Efficacy in Model Animal for Multi-organ Metastasis of Cancer

The human small cell lung carcinoma strain was injected into SCID mice, so that model animals for multi-organ metastasis of cancer, which exhibit tumor growth in multiple organs including bone, were produced. Using the model animals, the effect of mouse monoclonal antibodies against PTHrP (hereinafter, simply referred to as anti-PTHrP antibodies) on cancer metastasis was studied.

SCID mice which had been injected via caudal vein with the human small cell lung carcinoma strain SBC-5 were used as model animals. As described above, the mice injected with SBC-5 developed observable tumor growth in various organs including the lung, liver, kidney, and lymph nodes. That is, tumor nodules could be observed in these mice. Tumor growth was also observed in the bone tissue, and this could be observed by X-ray photography as a so-called punch-out image of bone absorption at the tumor growth site. The therapeutic effect of anti-PTHrP antibodies on cancer metastasis in SBC-5-injected model animals for multi-organ metastasis of cancer was evaluated using the number of tumor nodules in the lung, liver, kidney and lymph nodes and incidences of punch-out in the bone tissue as indices.

The model animal was produced as follows. SBC-5 was maintained by normal cell culturing using EMEM supplemented with 10% FBS. SCID mice were used. The mice were treated with TM-β1 antibodies to remove NK cells, and then injected via caudal vein with $1\times10^6$ cells, thereby producing model animals.

The drug efficacy of the anti-PTHrP antibody was examined as follows. Five experimental groups were established, consisting of a control group and 4 treated-groups which vary in respect of starting time of administration with anti-PTHrP antibodies. Administration was performed via caudal vein intravenously on days—1, 7, 14, 21 and 28 when day 0 was determined as a day of cell injection. The anti-PTHrP antibodies (200 mg/mouse) were administered to the treated groups, and PBS to the negative control group. Specifically, the anti-PTHrP antibodies were administered to 4 treated groups on days (i)—1, 7, 14, 21 and 28; (ii) 7, 14, 21 and 28; (iii) 14, 21 and 28; (iv) 21 and 28. Here, on a day for administration as described above, at which no anti-PTHrP antibody was administered, PBS was administered to these treated groups. On day 35, mice were dissected, and then the number of tumor nodules formed was counted. Further, the whole body of the mouse was subjected to X-ray photography, so that the number of incidences of punch-out was counted.

Figure 4A:
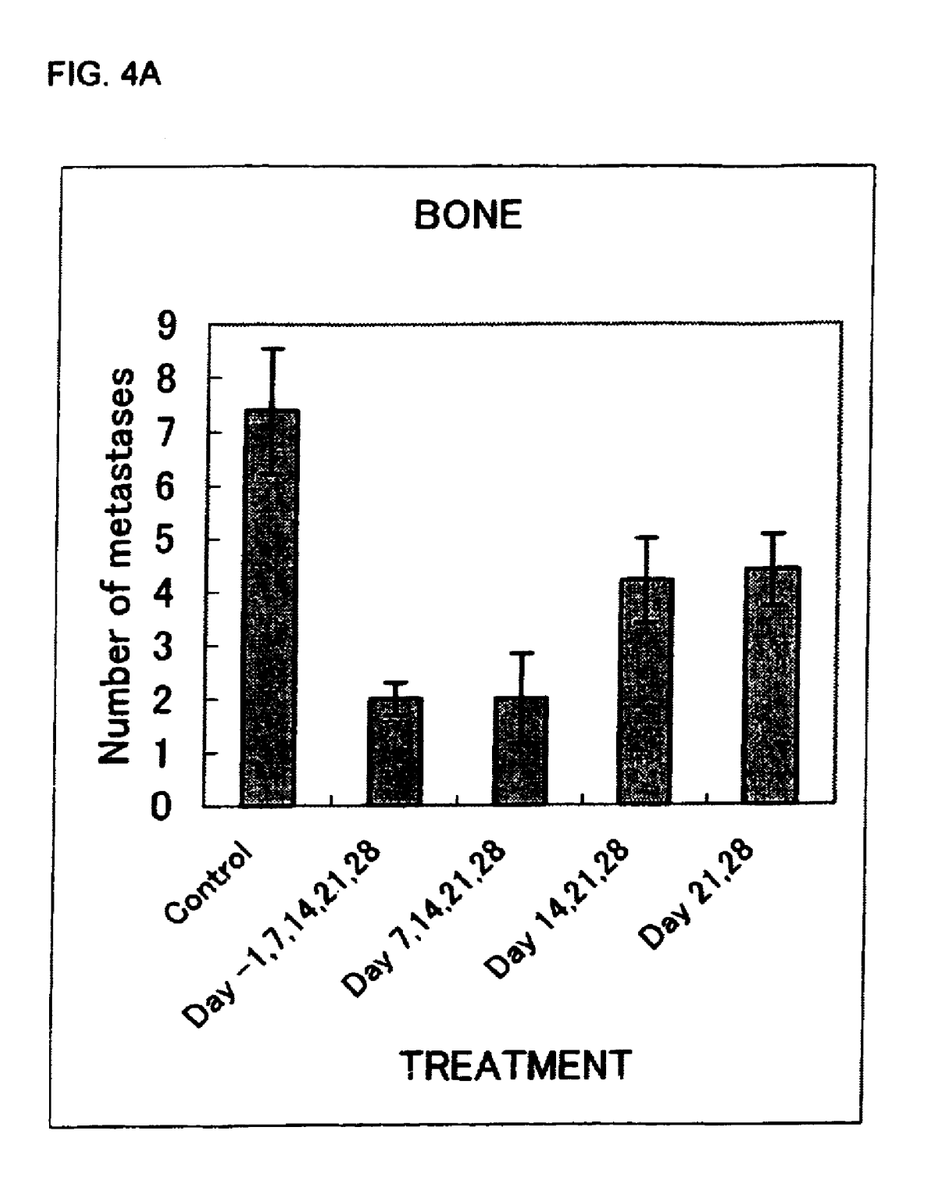
FIG. 4 shows the effect of anti-PTHrP antibodies on metastasis to the bone, lung, liver, kidney, and lymph nodes in model animals for multi-organ metastasis.
Figure 4B:
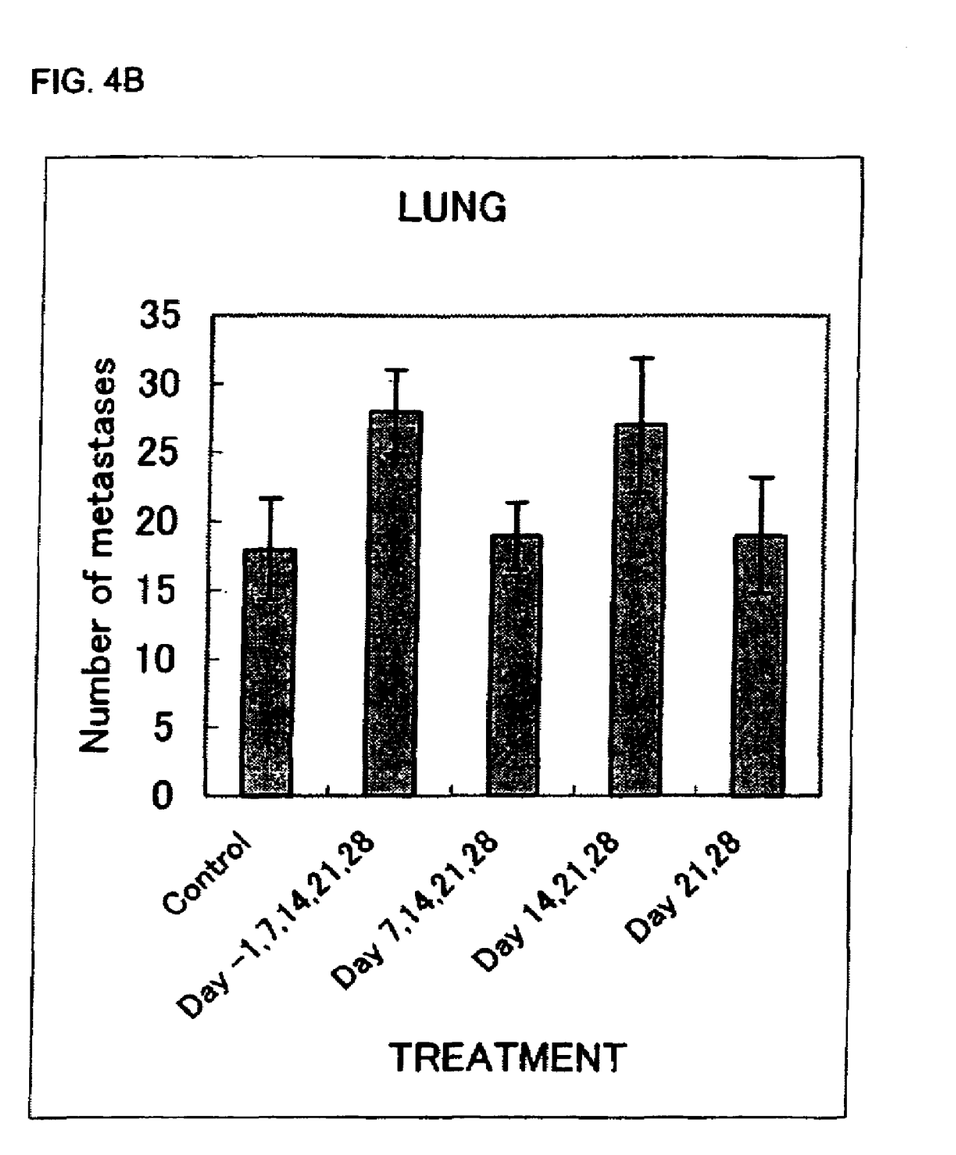
Figure 4C:
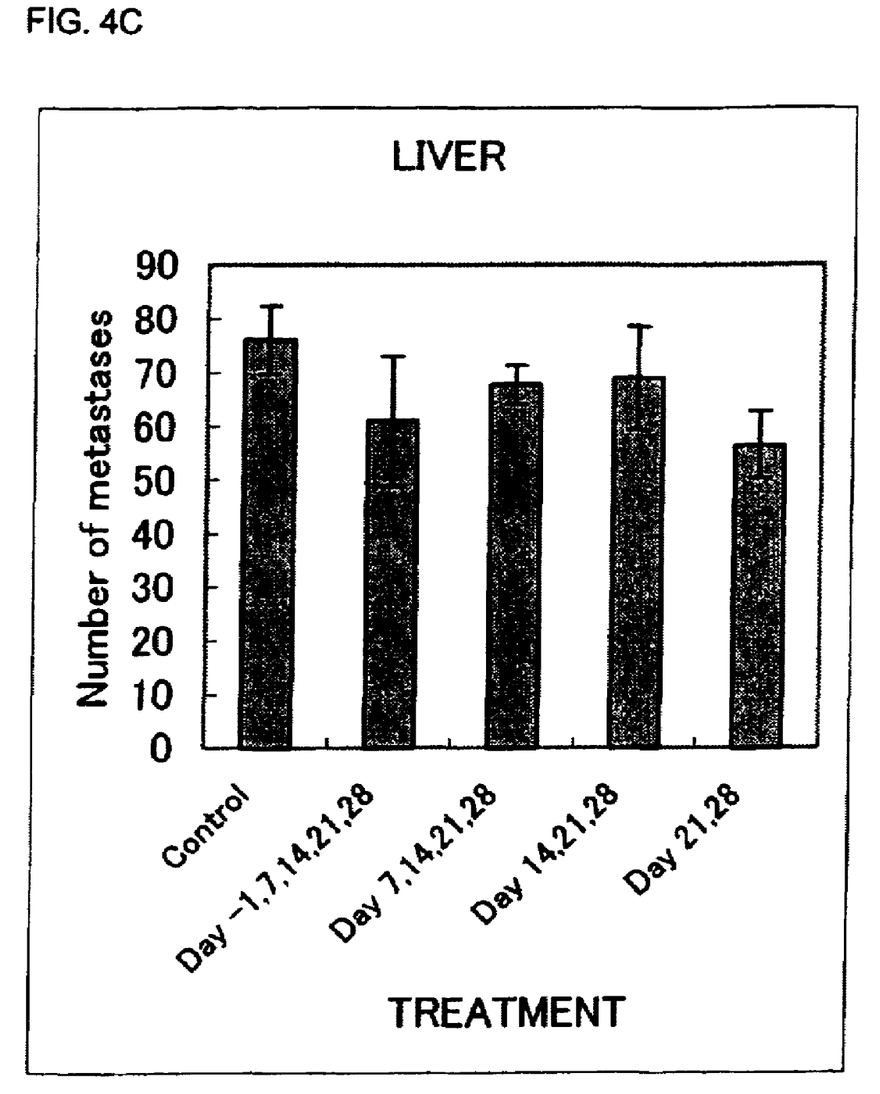
Figure 4D:
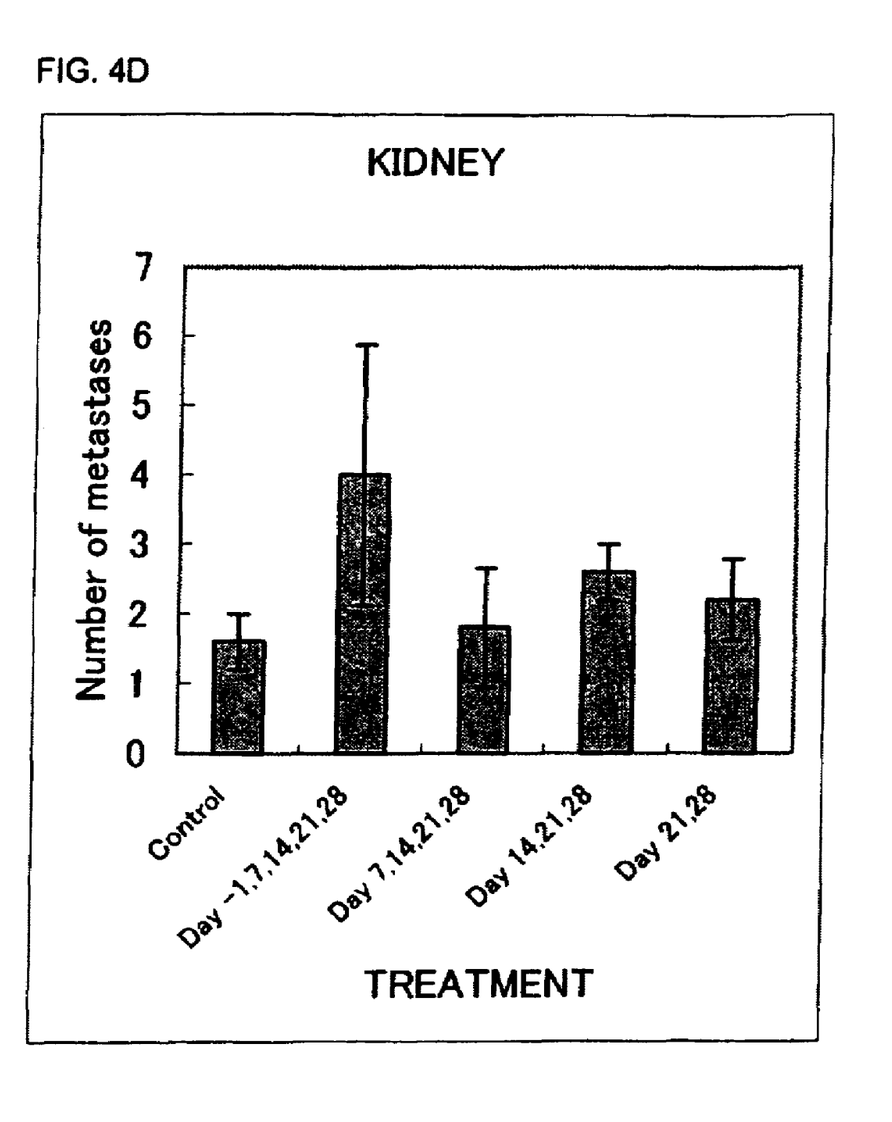
Figure 4E:
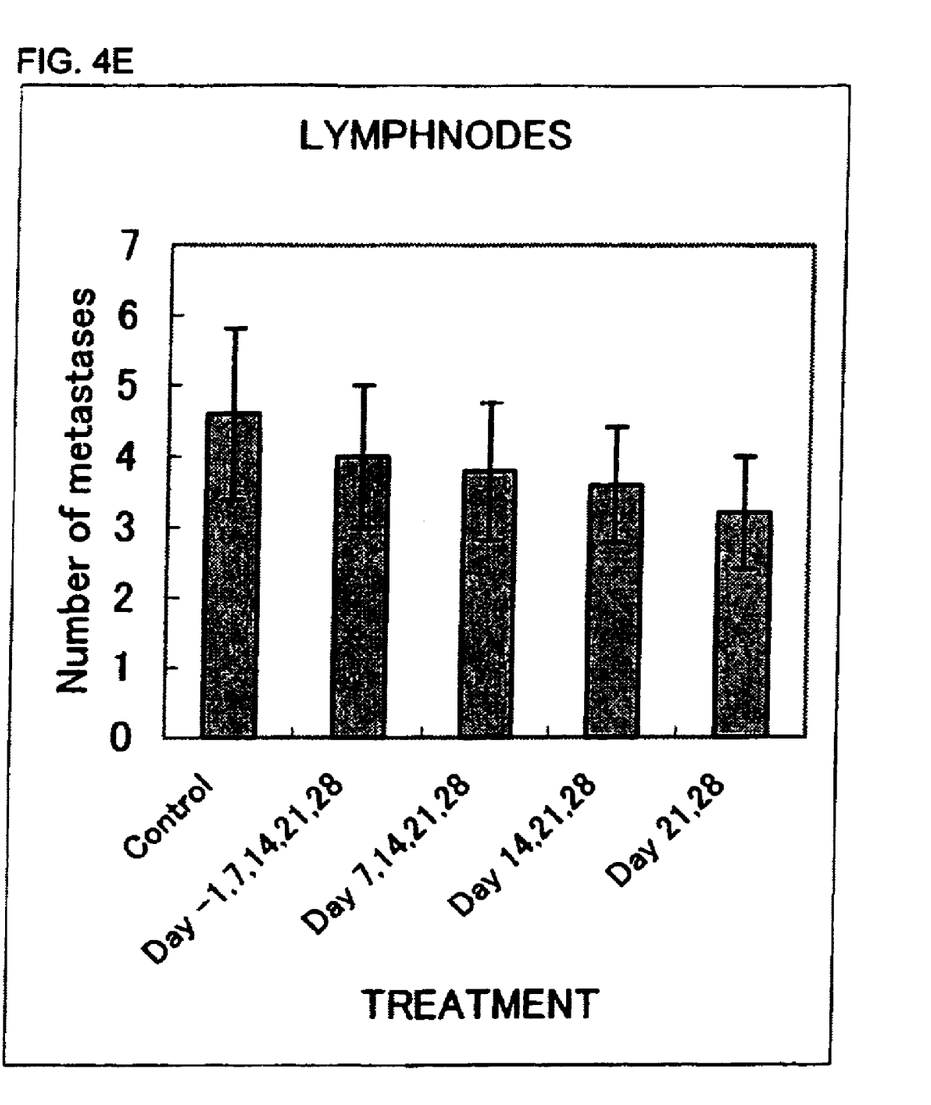

Compared to the control group, the anti-PTHrP antibody-administered groups showed a reduced number of incidences of punch-out in the bone (FIG. 4a). The earlier the start of administration with the anti-PTHrP antibodies, the more significant the effect that was observed. Changes in the number of tumor nodules formed were not observed in other organs (FIG. 4b–e). These results suggest that the anti-PTHrP antibody is useful in treating or preventing bone metastasis of cancer.

As described in detail above, we have established the bone metastasis model by inoculating tumor cells by intravenous injection. This model well simulates the features of human small cell lung carcinoma, such that the tumor cells in the recipient mice cause coincidence of osteolytic lesion (which causes paralysis) and multi-organ metastasis, and hypercalcemia. Moreover, our data suggest that PTHrP secreted from tumor cells plays an important role in the course of bone metastasis and hypercalcemia. Therefore, the bone metastasis model that we have developed enables simple screening of a novel agent for inhibiting and/or preventing bone metastasis, and is useful in elucidating the biological phenomenon of bone metastasis and in developing a novel treatment for lung cancer patients with multi-organ metastasis including bone metastasis.

The method of the present invention is economical because it introduces tumor cells by peripheral administration which does not usually result in the death of animals; the method is also ethically preferable because it does not sacrifice more than the necessary number of animals.

All publication, patents and patent application cited herein are incorporated herein by reference in their entirety for any purpose.

The invention claimed is:

1. A method for evaluating efficiencies of a treatment against bone metastasis of tumor cells, comprising:
applying a treatment to a subject bone metastasis model mouse, wherein the bone metastasis model mouse exhibits bone metastasis of tumor cells, wherein a suspension comprising single cells of human small cell lung carcinoma SBC-5 cells that induces bone metastasis has been introduced by intravenous administration, wherein the mouse is immunodeficient, and wherein the metastasis occurs in the mouse's own bone; and
comparing the size and/or extent of bone metastasis, and/or symptoms resulting from bone metastasis of the subject model mouse, with that of a control bone metastasis model mouse, wherein the treatment was not applied to the control mouse, and wherein differences between the subject mouse and the control mouse indicate the efficiency of the treatment.

2. A method for determining the effect of a test substance on bone metastasis, comprising:
administering the test substance to a subject bone metastasis model mouse, wherein the bone metastasis model mouse exhibits bone metastasis of tumor cells, wherein a suspension comprising single cells of human small cell lung carcinoma SBC-5 cells that induces bone metastasis has been introduced by intravenous administration, wherein the mouse is immunodeficient, and wherein the metastasis occurs in the mouse's own bone; and
comparing the size and/or extent of bone metastasis, and/or symptoms resulting from bone metastasis of the subject model mouse, with that of with a control bone metastasis model mouse, wherein the test substance was not administered to the control mouse, and wherein differences between the subject mouse and the control mouse indicate the effect of the test substance.

3. A method of screening a substance for inhibiting and/or preventing bone metastasis of tumor cells, comprising:
producing a model mouse exhibiting multi-organ metastasis of tumor cells including bone metastasis, wherein a suspension comprising single cells of human small cell lung carcinoma SBC-5 cells that induces multi-organ metastasis including bone metastasis has been introduced by intravenous administration, and wherein the mouse is immunodeficient;
administering a test substance to the model mouse; and
measuring inhibitory and/or preventive effect of the test substance on bone metastasis.

4. The method according to claim 3, wherein the test substance is a PTHrP antagonist, anti-PTHrP antibody, anti-PTHrP antibody analog or low molecular weight compound.

5. A method of evaluating efficiencies of a treatment against bone metastasis of tumor cells, comprising:
treating a subject model mouse exhibiting multi-organ metastasis of tumor cells including bone metastasis with the treatment, wherein a suspension comprising single cells of human small cell lung carcinoma SBC-5 cells that induces multi-organ metastasis including bone metastasis has been introduced by intravenous administration, and wherein the mouse is immunodeficient; and
comparing the size and/or extent of bone metastasis, and/or symptoms resulting from bone metastasis of the subject model mouse, with that of a control model mouse exhibiting multi-organ metastasis of tumor cells including bone metastasis, wherein the control mouse was not treated, and wherein differences between the subject mouse and the control mouse indicate the efficiency of the treatment.

6. A method of using a subject model mouse exhibiting multi-organ metastasis of tumor cells including bone metastasis for determining the effect of a test substance on bone metastasis, wherein a suspension comprising single cells of human small cell lung carcinoma SBC-5 cells that induces multi-organ metastasis including bone metastasis has been introduced by intravenous administration, and wherein the mouse is immunodeficient, comprising:
administering the test substance to the subject model mouse; and
comparing the size and/or extent of bone metastasis, and/or symptoms resulting from bone metastasis of the subject model mouse, with that of a control model mouse exhibiting multi-organ metastasis of tumor cells including bone metastasis, wherein the test substance was not administered to the control mouse.

7. The method according to claim 3, 5, or 6, wherein the multi-organ metastases include metastases to one or more organs selected from lung, liver, kidney, and lymph node.

8. The method according to claim 1 or 2, wherein the bone metastasis model mouse is a SCID mouse.

9. The method according to claim 8, wherein the mouse is a NK-cell depleted SCID mouse.

10. The method according to claim 3, 5, or 6, wherein the model mouse is a SCID mouse.

11. The method according to claim 10, wherein the mouse is a NK-cell depleted SCID mouse.

* * * * *

UNITED STATES PATENT AND TRADEMARK OFFICE
CERTIFICATE OF CORRECTION

| | | |
|---|---|---|
| PATENT NO. | : 7,135,609 B2 | Page 1 of 1 |
| APPLICATION NO. | : 10/143364 | |
| DATED | : November 14, 2006 | |
| INVENTOR(S) | : Saburo Sone and Toyokazu Miki | |

It is certified that error appears in the above-identified patent and that said Letters Patent is hereby corrected as shown below:

In claim 2, column 19, line 48, "with that of with a control" should read --with that of a control--.

Signed and Sealed this

Thirteenth Day of February, 2007

JON W. DUDAS
*Director of the United States Patent and Trademark Office*